United States Patent
Evanno et al.

(10) Patent No.: US 6,262,045 B1
(45) Date of Patent: Jul. 17, 2001

(54) 4-OXO-3,5-DIHYDRO-4H-PYRIDAZINO[4,5-B]-INDOLE-1-ACETAMIDE DERIVATIVES, THEIR PREPARATION AND THEIR APPLICATION IN THERAPY

(75) Inventors: Yannick Evanno, Bullion; Laurent Dubois, Gif sur Yvette; Mireille Sevrin, Paris; Frank Marguet, Verrières le Buisson; Jacques Froissant, Morée; Régine Bartsch, Fontenay aux Roses; Catherine Gille, Longjumeau, all of (FR)

(73) Assignee: Sanofi-Synthelabo, Paris (FR)

( * ) Notice: Subject to any disclaimer, the term of this patent is extended or adjusted under 35 U.S.C. 154(b) by 0 days.

(21) Appl. No.: 09/463,634

(22) PCT Filed: Jul. 28, 1998

(86) PCT No.: PCT/FR98/01667

§ 371 Date: Apr. 13, 2000

§ 102(e) Date: Apr. 13, 2000

(87) PCT Pub. No.: WO99/06406

PCT Pub. Date: Feb. 11, 1999

(30) Foreign Application Priority Data

Jul. 30, 1997 (FR) .................................... 97/09692

(51) Int. Cl.$^7$ ............... C07D 487/04; A61K 31/5025; A61P 25/12; A61P 25/22
(52) U.S. Cl. ................ 514/210.18; 514/233.2; 514/248; 544/115; 544/234
(58) Field of Search ............... 514/210.18, 248, 514/233.2; 544/115, 234

(56) References Cited

U.S. PATENT DOCUMENTS

| | | | |
|---|---|---|---|
| 4,985,560 | * | 1/1991 | Sabb et al. .............. 544/115 |
| 5,756,501 | * | 5/1998 | Sabb ...................... 514/248 |
| 6,075,021 | | 6/2000 | Evanno et al. .......... 514/232.8 |

FOREIGN PATENT DOCUMENTS 2 290 292    12/1995  (GB) .
WO 98/15552  4/1998   (WO) .

OTHER PUBLICATIONS

Goldstein, A. "Addiction:from Biology to Drug Policy", W.H. Freeman, 1994, p 3–5.*
Developments in the Treatment of Parkinson's Disease, no author listed, Drug Ther. Bull., 37(5) 1999, 36–40.*

* cited by examiner

Primary Examiner—Mukund J. Shah
Assistant Examiner—Thomas McKenzie
(74) Attorney, Agent, or Firm—Finnegan, Henderson, Farabow, Garrett & Dunner, L.L.P.

(57) ABSTRACT

Compounds of general formula (I)

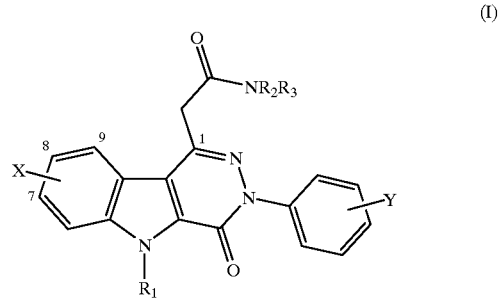

in which X represents a hydrogen or halogen atom or a methyl, methoxy or phenylmethoxy group, Y represents a hydrogen atom, 1 or 2 halogen atoms or a hydroxyl, methoxy, nitro or methyl group, $R_1$ represents a hydrogen atom or a ($C_1$–$C_4$)alkyl group, $R_2$ and $R_3$ each represent a hydrogen atom, a ($C_1$–$C_4$)alkyl group or a phenylmethyl group or else $R_2$ and $R_3$ form, with the nitrogen atom which carries them, an azetidinyl, pyrrolidinyl, 3-ethoxypyrrolidinyl, piperidinyl, morpholinyl, 4-methylpiperazinyl or 1,3-thiazolidinyl group. Application in therapeutics.

7 Claims, No Drawings

4-OXO-3,5-DIHYDRO-4H-PYRIDAZINO[4,5-B]-INDOLE-1-ACETAMIDE DERIVATIVES, THEIR PREPARATION AND THEIR APPLICATION IN THERAPY

This application is a national stage application of PCT/FR98/01667, filed Jul. 28, 1998, which claims priority to French patent application 97/09692, filed Jul. 30, 1997.

The subject-matter of the present invention is compounds of general formula (I)

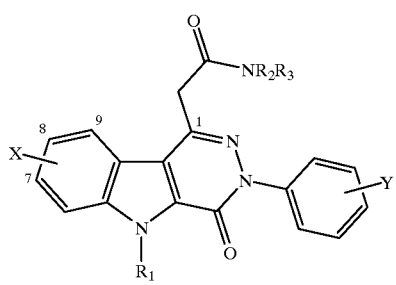

(I)

in which

X represents a hydrogen or halogen atom or a methyl, methoxy or phenylmethoxy group, Y represents a hydrogen atom, 1 or 2 halogen atoms or a hydroxyl, methoxy, nitro or methyl group, $R_1$ represents a hydrogen atom or a $(C_1-C_4)$alkyl group, $R_2$ and $R_3$ each represent, independently of one another, a hydrogen atom, a $(C_1-C_4)$alkyl group or a phenylmethyl group, or else $R_2$ and $R_3$ form, with the nitrogen atom which carries them, an azetidinyl, pyrrolidinyl, 3-ethoxypyrrolidinyl, piperidinyl, morpholinyl, 4-methylpiperazinyl or 1,3-thiazolidinyl group, the respective formulae of which are as follows:

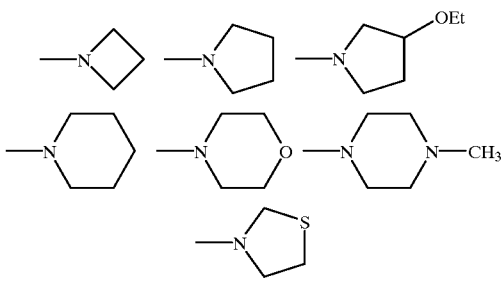

The preferred compounds are those in the general formula of which X is in the 8 or 9 position and represents a hydrogen or halogen atom, Y represents a hydrogen atom, $R_1$ represents a methyl or ethyl group, $R_2$ represents a hydrogen atom or a methyl group and $R_3$ represents a methyl group or else $R_2$ and $R_3$ form, with the nitrogen atom which carries them, an azetidinyl or pyrrolidinyl ring.

The compounds of general formula (I) can be prepared by processes illustrated in the following schemes.

According to Scheme 1, a compound of general formula (II), in which X and $R_1$ are as defined above and R' represents a $(C_1-C_4)$alkyl group, is reacted with oxalyl chloride, in an aprotic solvent, such as toluene, between 50° C. and the reflux temperature, the reaction intermediate is then treated at room temperature with an alcohol of general formula R"OH, in which R" represents a $(C_1-C_4)$alkyl group, in order to obtain the diester of general formula (III), or else the compound of general formula (II) is reacted with an alkyl chloroglyoxylate in a polar aprotic solvent, such as dichloromethane, at room temperature, in the presence of a Lewis acid, for example titanium tetrachloride, in order to obtain the diester of general formula (III).

The latter is subsequently treated in acetic acid, first at room temperature and then at the reflux temperature, with a phenylhydrazine optionally substituted by a Y group as defined above, in order to obtain an ester of general formula (IV). When $R_1$ represents an alkyl group, this ester is converted to the corresponding alcohol, of general formula (V), by reduction by means of a reducing agent, such as sodium borohydride, in a solvent, such as tetrahydrofuran, in the presence of an alcohol, for example methanol. This alcohol (V) is subsequently converted to the halogenated compound of general formula (VIII) by any reaction known to a person skilled in the art, either, for example, treatment with carbon tetrabromide in the presence of triphenylphosphine, in a solvent such as dichloromethane, or else by the action of a chlorinating agent, such as methanesulphonyl chloride, in a mixture of solvents, such as tetrahydrofuran and pyridine.

Scheme 1

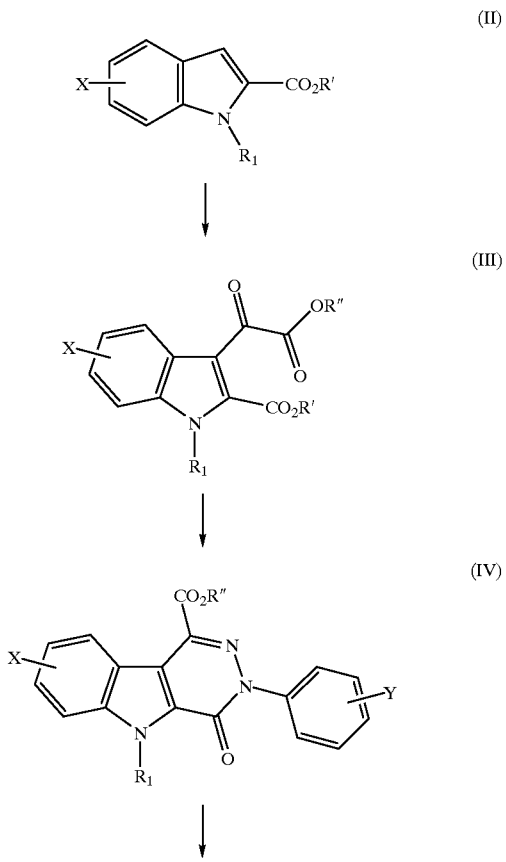

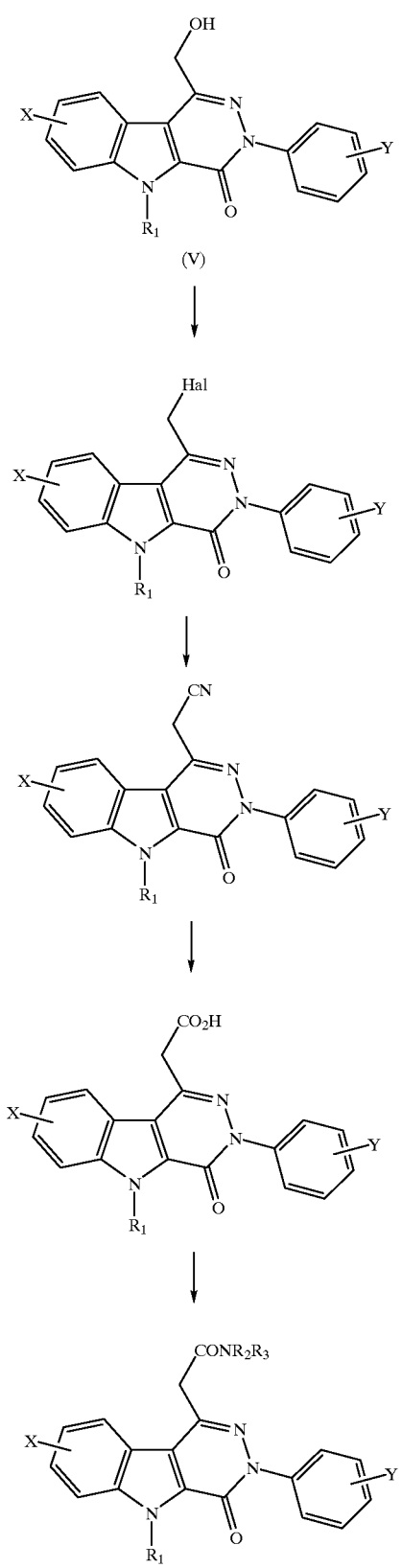

solvents, such as dimethylformamide and water, at a temperature of 20 to 80° C., or in a two-phase mixture, such as water and dichloromethane, between room temperature and the reflux temperature, in the presence of a phase transfer agent, in order to obtain the compound of general formula (IX).

An acidic hydrolysis is subsequently carried out, for example by using a mixture of acetic acid and of hydrochloric acid, at the reflux temperature, or else a basic hydrolysis is subsequently carried out, for example by using potassium hydroxide in a mixture of solvents, such as water and 2-methoxyethanol, at the reflux temperature, in order to obtain the compound of general formula (X).

This acid is subsequently converted to the secondary or tertiary amide of general formula (I) by reaction with an amine of general formula $HNR_2R_3$, in which $R_2$ and $R_3$ are as defined above, via the intermediacy, for example, of the imidazolide obtained by reaction with 1,1'-carbonylbis-1H-imidazole.

It is possible, if a final compound of general formula (I) in which $R_1$ represents hydrogen is desired, to convert a compound of general formula (IV) in which $R_1$ represents hydrogen to a compound of general formula (IV) in which $R_1$ represents a protective group, such as the methoxymethyl group, for example, by an alkylation reaction known to a person skilled in the art. The conversions according to Scheme 1 are continued until the compound of general formula (IX) is obtained and then an acidic hydrolysis of the latter, which at the same time removes the methoxymethyl protective group, results in a compound of general formula (X) in which $R_1$ represents a hydrogen atom.

According to Scheme 2, the compound of general formula (II) as defined above is converted to a compound of general formula (VI) by any method known to a person skilled in the art, for example by an electrophilic reaction in acidic medium. The latter is subsequently treated in acetic acid, first at room temperature and then at the reflux temperature, with a phenylhydrazine optionally substituted by a Y group as defined above. A compound of general formula (VII) is obtained, which is converted to the corresponding halogenated derivative of general formula (VIII) by a radical-type reaction, for example by using N-bromosuccinimide, in a solvent such as carbon tetrachloride, in the presence of an agent such as 2,2'-azobis(2-methylpropionitrile). The compound of general formula (VIII) is subsequently treated as described with respect to Scheme 1.

It is possible, if desired, to convert a compound of general formula (I) in which X represents a halogen atom to a compound of general formula (I) in which X represents a methyl group by any coupling reaction known to a person skilled in the art, for example by using tetramethyltin in the presence of a A nucleophilic substitution reaction with the cyanide ion is subsequently carried out, either in a mixture of polar Scheme 2

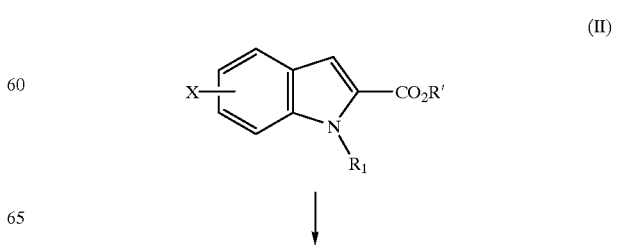

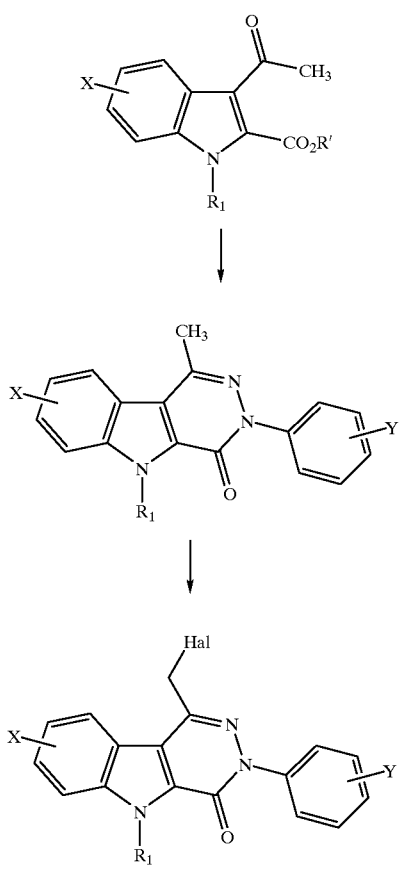

palladium complex.

Likewise, a compound of general formula (I), in which Y represents a methoxy group, can be converted to a compound in the formula of which Y represents a hydroxyl group by any known method, for example by the action of boron tribromide, in a chlorinated solvent, such as dichloromethane.

It is also possible, if desired, to convert a compound of general formula (I) in which X represents a chlorine atom to a compound of general formula (I) in which R represents hydrogen, for example by hydrogenation in the presence of palladium-on-charcoal.

According to Scheme 3, a compound of general formula (V), in which $R_1$ represents an alkyl group and X represents a chlorine atom, is converted to a compound of general formula (XI) by oxidation of the alcohol functional group, for example by using manganese dioxide in a solvent such as dichloromethane. The aldehyde (XI) is subsequently converted to a nitrile of general formula (XII) by reaction with (4-methylbenzenesulphonyl)methyl isocyanide ("TosMIC") in a solvent, such as 1,2-dimethoxyethane, in the presence of a base, such as potassium 1,1-dimethylethoxide. The nitrile (XII) is subsequently converted to an ester of general formula (XIII), in which R" represents a lower alkyl group, by the action of an acid, such as hydrogen chloride, in an alcoholic solvent of formula R"OH.

Finally, this ester (XIII) is converted to the secondary or tertiary amide of general formula (I) by reaction with an amine of general formula $HNR_2R_3$, in which $R_2$ and $R_3$ are as defined above, for example in the presence of a trialkylaluminium derivative, in a solvent such as toluene.

The starting compounds of general formula (II), mainly when $R_1$ represents hydrogen, are described in the literature. If desired, the compound in the formula of which $R_1$ represents hydrogen can be subjected to an alkylation reaction in order to result in a compound in the formula of which $R_1$ represents an alkyl group.

The examples which will follow illustrate the preparation of some compounds according to the invention. The elemental microanalyses and the I.R. and N.M.R. spectra confirm the structures of the compounds obtained.

The numbers shown between brackets in the titles of the examples correspond to those in the 1st column of Table 1 given later.

In the names of the compounds, the dash "-" forms part of the word and the dash "$_{13}$" is only used for the line end break; it is to be omitted in the absence of a break and must not be replaced either by a hyphen or by a space.

EXAMPLE 1

(Compound No. 9)

5-Ethyl-8-fluoro-N,N-dimethyl-4-oxo-3-phenyl-3,5-dihydro-4H-pyridazino[4,5-b]indole-1-acetamide 1.1. Ethyl 1-ethyl-5-fluoro-1H-indole-2-carboxylate A suspension of 3.8 g (95 mmol) of 60% sodium hydride Scheme 3

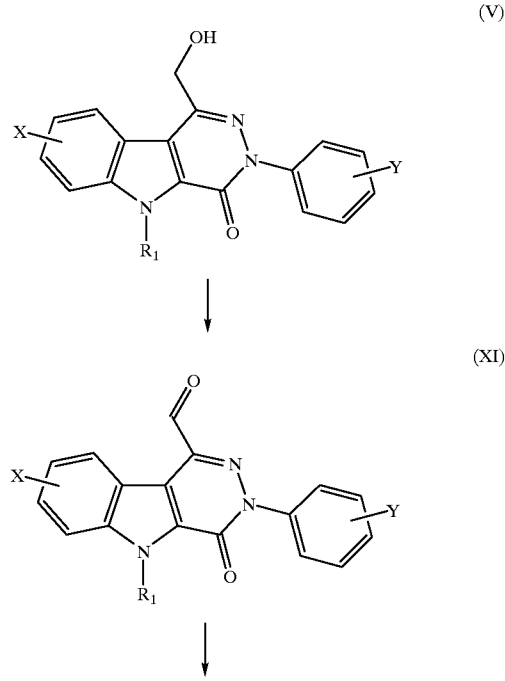

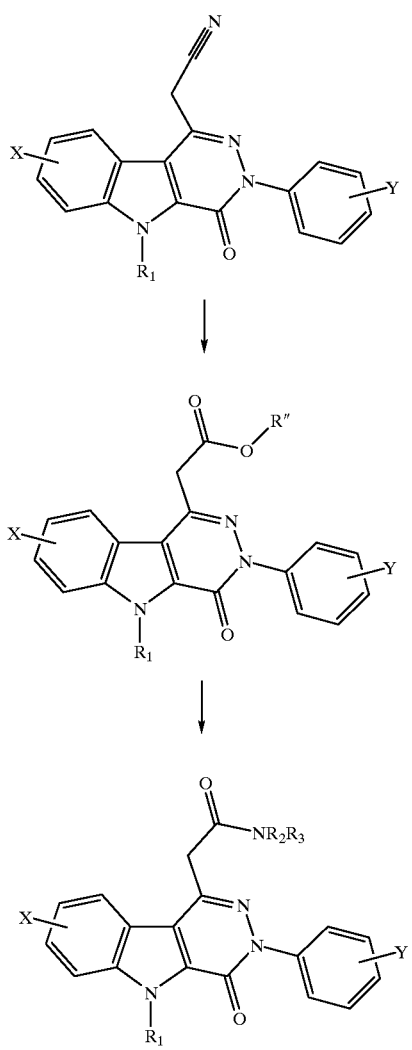

(washed beforehand with petroleum ether) and of 15 g (72.4 mmol) of ethyl 5-fluoro-1H-indole-2-carboxylate in 100 ml of dimethylformamide is stirred for 2 h at room temperature. 7.5 ml (93.7 mmol) of iodoethane, in solution in 20 ml of dimethylformamide, are subsequently added. After stirring for 10 h at room temperature, the reaction mixture is poured onto ice-cold water. It is extracted with diethyl ether. The organic phase is washed several times with water, dried over magnesium sulphate and concentrated under reduced pressure. 17 g (72 mmol) of a yellow oil are obtained, which oil is used as is in the following stage.

1.2. Methyl 2-(ethoxycarbonyl)-1-ethyl-5-fluoro-α-oxo-1H-indole-3-acetate

A solution of 17 g (72 mmol) of ethyl 1-ethyl-5-fluoro-1H-indole-2-carboxylate and of 7.4 ml (84.5 mmol) of oxalyl chloride in 500 ml of toluene is heated at reflux for 6 h. An additional 5 ml (57 mmol) of oxalyl chloride are added, heating is carried out for 1 h at reflux and the mixture is allowed to return to room temperature. 200 ml of methanol are added, the mixture is stirred for 10 min and the solvents are evaporated under reduced pressure. The resulting oil is taken up in dichloromethane and the organic phase is washed with water, dried over magnesium sulphate and concentrated under reduced pressure. After recrystallizing from propan-2-ol, 14 g (43.6 mmol) of compound are obtained in the form of a white solid.

1.3. Methyl 5-ethyl-8-fluoro-4-oxo-3-phenyl-3,5-dihydro-4H-pyridazino[4,5-b]indole-1-carboxylate 18.4 ml (187.2 mmol) of phenylhydrazine are added, at room temperature, to a solution of 14 g (43.6 mmol) of methyl 2-(ethoxycarbonyl)-1-ethyl-5-fluoro-α-oxo-1H-indole-3-acetate in 150 ml of acetic acid and the reaction mixture is stirred for 30 min at room temperature and then for 2 h at reflux. The mixture is cooled, 100 ml of water are added and an insoluble material is separated by filtration, the insoluble material being washed on sintered glass with a 70/30 mixture of water and acetone. 10.5 g (28.6 mmol) of white solid are thus isolated, which solid is used as is in the following stage.

1.4. 5-Ethyl-8-fluoro-1-(hydroxymethyl)-3-phenyl-3,5-dihydro-4H-pyridazino[4,5-b]indol-4-one 5.1 g (135 mmol) of sodium borohydride are added, in several portions and at room temperature, to a solution of 10 g (27.3 mmol) of methyl 5-ethyl-8-fluoro-4-oxo-3-phenyl-3,5-dihydro-4H-pyridazino[4,5-b]indole-1-carboxylate in 200 ml of tetrahydrofuran and 5.8 ml of methanol and the mixture is stirred for 4 h at reflux. The mixture is poured onto an ice-cold 0.1N hydrochloric acid solution, an insoluble material is separated by filtration, the insoluble material being washed with water and with diethyl ether, on sintered glass, and then it is dried. 7.2 g (21.4 mmol) of compound are isolated in the form of a white solid which is used as is in the following stage.

1.5. 1-(Bromomethyl)-5-ethyl-8-fluoro-3-phenyl-3,5-dihydro-4H-pyridazino[4,5-b]indol-4-one 11.5 g (43.84 mmol) of triphenylphosphine are added, in several portions, to a solution of 7.2 g (21.4 mmol) of 5-ethyl-8-fluoro-1-(hydroxymethyl)-3-phenyl-3,5-dihydro-4H-pyridazino[4,5-b]indol-4-one and of 15.3 g (46.13 mmol) of carbon tetrabromide in 500 ml of dichloromethane and the solution is stirred for 12 h at room temperature. The mixture is concentrated to 1/3 under reduced pressure and the precipitate is collected by filtration, washed with ether and dried under reduced pressure. 4 g (10 mmol) of solid are obtained. 300 ml of dichloromethane, 8 g (24.1 mmol) of carbon tetrabromide and 5 g (19.06 mmol) of triphenylphosphine are added to the mother liquors and the solution is stirred for 12 h at room temperature and then concentrated to 1/3. The precipitate is collected by filtration, washed with ether and dried under reduced pressure. 3.2 g (8 mmol) of additional solid are obtained.

1.6. 5-Ethyl-8-fluoro-4-oxo-3-phenyl-3,5-dihydro-4H-pyridazino[4,5-b]indole-1-acetonitrile A two-phase mixture of 7.2 g (18 mmol) of 1-(bromomethyl)-5-ethyl-8-fluoro-3-phenyl-3,5-dihydro-4H-pyridazino[4,5-b]indol-4-one, of 3.53 g (72 mmol) of sodium cyanide and of 0.58 g (1.8 mmol) of tetrabutylammonium bromide in 300 ml of dichloromethane and 150 ml of water is stirred vigorously for 12 h. The organic phase is separated, washed several times with water, dried over magnesium sulphate and concentrated under reduced pressure. 5.8 g (16.8 mmol) of compound are isolated, which compound is used as is in the following stage.

1.7. 5-Ethyl-8-fluoro-4-oxo-3-phenyl-3,5-dihydro-4H-pyridazino[4,5-b]indole-1-acetic acid A solution of 5.8 g (16.8 mmol) of 5-ethyl-8-fluoro-4-oxo-3-phenyl-3,5-dihydro-4H-pyridazino[4,5-b]indole-1- acetonitrile in 200 ml of a 1/1 mixture of concentrated hydrochloric acid and of glacial acetic acid is heated at reflux for 2 h. The solution is cooled, 100 ml of water are added and the insoluble material is collected by filtration and washed copiously with water and with ether on sintered glass. After drying in an oven, 5.2 g (15 mmol) of a white solid are obtained, which solid is used as is in the following stage.

1.8. 5-Ethyl-8-fluoro-N,N-dimethyl-4-oxo-3-phenyl-3,5-dihydro-4H-pyridazino[4,5-b]indole-1-acetamide A suspension of 1 g (2.73 mmol) of 5-ethyl-8-fluoro-4-oxo-3-phenyl-3,5-dihydro-4H-pyridazino[4,5-b]indole-1-acetic acid and of 0.7 g (4.3 mmol) of 1,1'-carbonylbis-1H-imidazole in 200 ml of tetrahydrofuran is stirred for 3 h at 50° C. The reaction mixture is cooled to 25° C., an excess of liquefied dimethylamine is added and the reaction mixture is stirred for 12 h at room temperature. It is concentrated under reduced pressure, 100 ml of dichloromethane and 100 ml of water are added and the organic phase is separated, washed with water, dried over magnesium sulphate and concentrated under reduced pressure. The resulting oil crystallizes from ether. After filtering and recrystallizing from ethyl acetate, 0.75 g (1.9 mmol) of white crystals is isolated.

Melting point: 183–184° C.

EXAMPLE 2
(Compound No. 25)

1-[2-(8-Chloro-5-methyl-4-oxo-3-phenyl-3,5-dihydro-4H-pyridazino[4,5-b]indol-1-yl)-1-oxoethyl]pyrrolidine 2.1. Methyl 5-chloro-2-(ethoxycarbonyl)-1-methyl-α-oxo-1H-indole-3-acetate 15 ml (170 mmol) of oxalyl chloride are added to a solution of 31.5 g (133 mmol) of ethyl 5-chloro-1-methyl-1H-indole-2-carboxylate in 100 ml of toluene heated to 60° C. and the mixture is heated at reflux for 1 h.

The solution is cooled, 50 ml of methanol are added, the mixture is concentrated under reduced pressure and the residue is taken up in 100 ml of dichloromethane and 50 ml of water, sodium hydrogencarbonate is added, the organic phase is separated and dried over magnesium sulphate, the solvents are evaporated under reduced pressure, the residue is triturated in ether and the precipitate is collected by filtration and dried under reduced pressure. 19 g (59 mmol) of solid are obtained.

Melting point: 119–120° C.

2.2. Methyl 8-chloro-5-methyl-4-oxo-3-phenyl-3,5-dihydro-4H-pyridazino[4,5-b]indole-1-carboxylate A solution of 19 g (59 mmol) of methyl 5-chloro-2-(ethoxycarbonyl)-1-methyl-α-oxo-1H-indole-3-acetate and 26 g (240 mmol) of phenylhydrazine in 250 ml of acetic acid is heated at reflux for 2 h. The mixture is cooled, 250 ml of a 1/1 mixture of water and of acetone are added and the mixture is left standing at 4° C. for 15 h. The precipitate is collected by filtration, washed with water and with acetone and dried under reduced pressure. 17.4 g (47 mmol) of solid are obtained.

Melting point: 265–266° C.

2.3. 8-Chloro-1-(hydroxymethyl)-5-methyl-3-phenyl-3,5-dihydro-4H-pyridazino[4,5-b]indol-4-one A solution of 17.2 g (47 mmol) of methyl 8-chloro-5-methyl-4-oxo-3-phenyl-3,5-dihydro-4H-pyridazino[4,5-b]indole-1-carboxylate, of 8.7 g (230 mmol) of sodium borohydride and of 9.4 ml (230 mmol) of methanol in 300 ml of tetrahydrofuran is heated at reflux for 4 h. The mixture is cooled and poured onto a stirred solution of 100 ml of 2N hydrochloric acid and 100 ml of dichloromethane. The precipitate is collected by filtration, washed with water and dichloromethane and dried under reduced pressure. 15 g (44 mmol) of solid are obtained.

Melting point: 278–280° C.

2.4. 1-(Bromomethyl)-8-chloro-5-methyl-3-phenyl-3,5-dihydro-4H-pyridazino[4,5-b]indol-4-one The preparation is carried out as in Example 1.5, from 15 g (44 mmol) of 8-chloro-1-(hydroxymethyl)-5-methyl-3-phenyl-3,5-dihydro-4H-pyridazino[4,5-b]indol-4-one. After several treatments and purifications by silica gel chromatography, 15 g (37 mmol) of solid are isolated.

Melting point: 253–254° C.

2.5. 8-Chloro-5-methyl-4-oxo-3-phenyl-3,5-dihydro-4H-pyridazino[4,5-b]indole-1-acetonitrile The preparation is carried out as in Example 1.6, from 12.5 g (3 mmol) of 1-(bromomethyl)-8-chloro-5-methyl-3-phenyl-3,5-dihydro-4H-pyridazino[4,5-b]indol-4-one in a mixture of chloroform and water. After purification on a column of silica gel, 10 g (28 mmol) of solid are obtained.

Melting point: 230° C.

2.6. 8-Chloro-5-methyl-4-oxo-3-phenyl-3,5-dihydro-4H-pyridazino[4,5-b]indole-1-acetic acid A solution of 10 g (28 mmol) of 8-chloro-5-methyl-4-oxo-3-phenyl-3,5-dihydro-4H-pyridazino[4,5-b]indole-1-acetonitrile in a mixture of 200 ml of concentrated hydrochloric acid and of 200 ml of acetic acid is heated at 100° C. for 4 h. The solution is concentrated under reduced pressure, the residue is taken up in 250 ml of water and the precipitate is collected by filtration. It is washed with water and dried under reduced pressure. 10.2 g (27 mmol) of solid are obtained.

Melting point: 206–208° C.

2.7. 1-[2-(8-Chloro-5-methyl-4-oxo-3-phenyl-3,5-dihydro-4H-pyridazino[4,5-b]indol-1-yl)-1-oxoethyl]pyrrolidine A solution of 1.5 g (4 mmol) of 8-chloro-5-methyl-4-oxo-3-phenyl-3,5-dihydro-4H-pyridazino[4,5-b]indole-1-acetic acid and of 1.2 g (7.4 mmol) of 1,1'-carbonylbis-1H-imidazole in tetrahydrofuran is stirred for 1 h at 50° C. The mixture is cooled and an excess of pyrrolidine is added. After stirring for 15 h, the precipitate is collected by filtration, washed with water and with ether and recrystallized from propan-2-ol. 0.65 g (1.5 mmol) of solid is obtained.

Melting point: 261–262° C.

EXAMPLE 3
(Compound No. 27)

N,N,5-Trimethyl-4-oxo-3-phenyl-3,5-dihydro-4H-pyridazino[4,5-b]indole-1-acetamide 3.1. 5-Methyl-4-oxo-3-phenyl-3,5-dihydro-4H-pyridazino[4,5-b]indole-1-acetic acid A solution of 3.3 g (9 mmol) of 8-chloro-5-methyl-4-oxo-3-phenyl-3,5-dihydro-4H-pyridazino[4,5-b]indole-1-acetic acid, of 2.8 g (44 mmol) of ammonium formate and of 1.8 g of 10% palladium-on-charcoal in 500 ml of ethanol is heated at reflux for 5 h. The reaction mixture is cooled, dichloromethane is added, the catalyst is removed by filtration through diatomaceous earth and the solvent is evaporated under reduced pressure. 3 g (9 mmol) of compound are obtained, which compound is used as is in the following stage.

3.2. N,N,5-Trimethyl-4-oxo-3-phenyl-3,5-dihydro-4H-pyridazino[4,5-b]indole-1-acetamide A suspension of 1 g (3 mmol) of 5-methyl-4-oxo-3-phenyl-3,5-dihydro-4H-pyridazino[4,5-b]indole-1-acetic acid and of 0.7 g (4.3 mmol) of 1,1'-carbonylbis-1H-imidazole in 200 ml of tetrahydrofuran is stirred for 2 h at 60° C. The reaction mixture is cooled to 25° C., an excess of liquefied dimethylamine in solution in tetrahydrofuran is added and the reaction mixture is stirred for 72 h at room temperature. It is concentrated under reduced pressure, 300 ml of water are added and the precipitate is collected by filtration, washed with water and with ether and recrystallized from propan-2-ol. 0.75 g (2 mmol) of solid is isolated.

Melting point: 214–215° C.

EXAMPLE 4
(Compound No. 26)

1-[2-(5-Methyl-4-oxo-3-phenyl-3,5-dihydro-4H-pyridazino[4,5-b]indol-1-yl)-1-oxoethyl]pyrrolidine The preparation is carried out as in Example 3.2, from 1 g (3 mmol) of 5-methyl-4-oxo-3-phenyl-3,5-dihydro-4H-pyridazino[4,5-b]indole-1-acetic acid and from excess pyrrolidine. The product is recrystallized from propan-2-ol. 0.5 g (1.3 mmol) of solid is obtained.

Melting point: 214–215° C.

EXAMPLE 5
(Compound No. 31)

1-[2-(9-Bromo-5-methyl-4-oxo-3-phenyl-3,5-dihydro-4H-pyridazino[4,5-b]indol-1-yl)-1-oxoethyl]pyrrolidine

5.1. Methyl 2-azido-3-(2-bromophenyl)prop-2-enoate

A solution of 75 ml (624 mmol) of 2-bromobenzaldehyde and of 252 g (2.2 mmol) of methyl azidoacetate in 160 ml of methanol is added dropwise over 3 h, at a temperature of −10 to −8° C., under nitrogen and with mechanical stirring, to a solution of 476 ml of sodium methoxide (30% in methanol) in 950 ml of methanol. Stirring is maintained for 2 h at a temperature below 5° C. The mixture is poured onto 1.5 kg of ice. The precipitate is collected by filtration, washed with water and dried under reduced pressure with light excluded. 116 g (0.41 mol) of solid are obtained, which solid is used quickly in the following stage.

5.2. Methyl 4-bromo-1H-indole-2-carboxylate

A solution of 116 g (0.41 mol) of methyl 2-azido-3-(2-bromophenyl)prop-2-enoate in 1.5 l of toluene is added dropwise over 4 h, with mechanical stirring, to a solution of 2 l of toluene heated to reflux and reflux is maintained for an additional 1 h. The solvent is evaporated under reduced pressure and the residue is taken up in 2 l of cyclohexane. The precipitate is collected by filtration, washed with toluene and dried under reduced pressure 37.85 g (149 mmol) of product are isolated. The mother liquors are concentrated under reduced pressure and the residue is purified by chromatography on a column of silica gel. 12.2 g (48 mmol) of additional product are isolated.

5.3. Methyl 4-bromo-1-methyl-1H-indole-2-carboxylate

The preparation is carried out as in Example 1.1, from 20 g (79 mmol) of methyl 4-bromo-1H-indole-2-carboxylate, from 3.8 g of 60% sodium hydride and from 6 ml of iodomethane. After reaction, the solvent is evaporated under reduced pressure and the residue is taken up in water. The mixture is extracted with ethyl acetate. The organic phase is dried and the solvent is evaporated under reduced pressure. The product is dried under reduced pressure. 20.6 g (77 mmol) of solid are obtained.

Melting point: 85–86° C.

5.4. Methyl 3-acetyl-4-bromo-1-methyl-1H-indole-2-carboxylate 33 ml of trifluoroacetic anhydride are added to a solution of 13.2 ml of acetic acid, of 1.6 ml of phosphoric acid and of 170 ml of acetonitrile, stirring is carried out for 10 min at room temperature and a solution of 20.6 g (77 mmol) of methyl 4-bromo-1-methyl-1H-indole-2-carboxylate in 120 ml of acetonitrile is added. The mixture is stirred for 4 h at room temperature and is poured onto water and extracted with ether. The organic phase is dried over sodium sulphate, the solvent is evaporated under reduced pressure and the residue is taken up in a mixture of cyclohexane and of dichloromethane. The precipitate is collected by filtration, washed with ether and dried under reduced pressure. 18.8 g (61 mmol) of product are obtained. The mother liquors are concentrated and the residue is purified by chromatography on a column of silica gel. 3.2 g (10 mmol) of additional product are isolated.

Melting point 128° C.

5.5. 9-Bromo-1,5-dimethyl-3-phenyl-3,5-dihydro-4H-pyridazino[4,5-b]indol-4-one 22 g (71 mmol) of methyl 3-acetyl-4-bromo-1-methyl-1H-indole-2-carboxylate are dissolved with heating in 350 ml of acetic acid. 30 ml (300 mmol) of phenylhydrazine are added, stirring is carried out for 1 h at room temperature and the reaction mixture is heated at reflux for 5 h, at room temperature for 15 h and then again at reflux for 7 h. 28 ml of phenylhydrazine are added and the process is repeated. The mixture is concentrated under reduced pressure, the residue is taken up in water and the precipitate is collected by filtration, washed with water and dried under reduced pressure. It is purified by chromatography on a column of silica gel. 11.1 g (30 mmol) of product are isolated.

Melting point: 189–190° C.

5.6. 9-Bromo-1-(bromomethyl)-5-methyl-3-phenyl-3,5-dihydro-4H-pyridazino[4,5-b]indol-4-one A solution of 10.1 g (27.1 mmol) of 9-bromo-1,5-dimethyl-3-phenyl-3,5-dihydro-4H-pyridazino[4,5-b]indol-4-one, of 6 g (34 mmol) of N-bromosuccinimide and of 0.46 g (2.8 mmol) of 2,2'-azobis(2-methylpropionitrile) is heated at reflux for 5 h. 3 g (17 mmol) of N-bromosuccinimide and 0.23 g (1.4 mmol) of 2,2'-azobis(2-methylpropionitrile) are again added. The mixture is heated at reflux for 2 h, left at room temperature for 15 h and again heated at reflux for 5 h. The mixture is concentrated under reduced pressure and the residue is taken up in water and extracted with ethyl acetate. The organic phase is dried, the solvent is evaporated under reduced pressure and the residue is purified by chromatography on a column of silica gel. 5.9 g (13 mmol) of product are isolated.

5.7. 9-Bromo-5-methyl-4-oxo-3-phenyl-3,5-dihydro-4H-pyridazino[4,5-b]indole-1-acetonitrile A solution of 6.4 g (14.3 mmol) of 9-bromo-1-(bromomethyl)-5-methyl-3-phenyl-3,5-dihydro-4H-pyridazino[4,5-b]indol-4-one, of 3.6 g (73 mmol) of sodium cyanide and of 0.57 g (1 mmol) of tetrabutylammonium bromide in a mixture of 170 ml of dichloromethane and of 85 ml of water is heated at reflux for 3 h with mechanical stirring. Separation is carried out by settling and the reaction mixture is extracted with dichloromethane. The organic phase is washed with water and dried over sodium sulphate and the solvent is evaporated under reduced pressure. 5.6 g (14.2 mmol) of product are obtained, which product is used as is in the following stage.

5.8. 9-Bromo-5-methyl-4-oxo-3-phenyl-3,5-dihydro-4H-pyridazino[4,5-b]indole-1-acetic acid A solution of 4.8 g (12.2 mmol) of 9-bromo-5-methyl-4-oxo-3-phenyl-3,5-dihydro-4H-pyridazino[4,5-b]indole-1-acetonitrile in a mixture of 190 ml of acetic acid and of 50 ml of concentrated hydrochloric acid is heated at reflux for 6 h. The solution is concentrated under reduced pressure and the residue is taken up in a mixture of dichloromethane and of water. Basification is carried out with 30% sodium hydroxide solution, separation is carried out by settling and extraction is carried out with dichloromethane. The aqueous phase is acidified with concentrated hydrochloric acid while cooling with an ice bath. The precipitate is collected by filtration, washed with water and dried under reduced pressure. 3.1 g (7.5 mmol) of solid are obtained.

5.9. 1-[2-(9-Bromo-5-methyl-4-oxo-3-phenyl-3,5-dihydro-4H-pyridazino[4,5-b]indol-1-yl)-1-oxoethyl]pyrrolidine The preparation is carried out as in Example 3.2, from 3.1 g (7.5 mmol) of 9-bromo-5-methyl-4-oxo-3-phenyl-3,5-dihydro-4H-pyridazino[4,5-b]indole-1-acetic acid, from 1.4 g of 1,1'-carbonylbis-1H-imidazole and from 0.7 ml of pyrrolidine. After reaction, water is added and the precipitate is collected by filtration and dried under reduced pressure. It is recrystallized from propan-2-ol and washed with ether and pentane. It is dried under reduced pressure. 2.3 g (4.9 mmol) of solid are obtained.

Melting point: 209–210° C.

EXAMPLE 6
(Compound No. 11)

9-Bromo-5-methyl-N-methyl-4-oxo-3-phenyl-3,5-dihydro-4H-pyridazino[4,5-b]indole-1-acetamide The preparation is carried out as in Example 3.2, from 0.78 g (1.9 mmol) of 9-bromo-5-methyl-4-oxo-3-phenyl-3,5-dihydro-4H-pyridazino[4,5-b]indole-1-acetic acid. The product is recrystallized from propan-2-ol. 0.57 g (1.3 mmol) of solid is obtained.

Melting point: 267–268° C.

EXAMPLE 7
(Compound No. 38)

1-[2-(5,9-Dimethyl-4-oxo-3-phenyl-3,5-dihydro-4H-pyridazino[4,5-b]indol-1-yl)-1-oxoethyl]pyrrolidine pyridazino[4,5-b]indol-1-yl)-1-oxoethyl]pyrrolidine A solution of 1.2 g (2.6 mmol) of 1-[2-(9-bromo-5-methyl-4-oxo-3-phenyl-3,5-dihydro-4H-pyridazino[4,5-b]indol-1-yl)-1-oxoethyl]pyrrolidine, of 0.22 g (0.3 mmol) of bis(triphenylphosphine)palladium(II) chloride, of 0.41 g (1.55 mmol) of triphenylphosphine and of 1.5 ml (10.3 mmol) of tetramethyltin in 15 ml of dimethylformamide is heated at 120° C. for 18 h in a sealed tube. The mixture is concentrated under reduced pressure and the residue is taken up in dichloromethane and a sodium hydrogencarbonate solution. The organic phase is washed with a 10% potassium fluoride solution and dried over sodium sulphate, the solvent is evaporated under reduced pressure and the residue is purified by chromatography on a column of silica gel. The product is recrystallized from propan-2-ol, washed with ether and with pentane and dried under reduced pressure. 0.82 g (2 mmol) of solid is obtained.

Melting point: 214–215° C.

EXAMPLE 8
(Compound No. 23)

1-[2-(5-Methyl-4-oxo-3-phenyl-8-(phenylmethoxy)-3,5-dihydro-4H-pyridazino[4,5-b]indol-1-yl)-1-oxoethyl]pyrrolidine

8.1. 5-Methyl-4-oxo-3-phenyl-8-(phenylmethoxy)-3,5-dihydro-4H-pyridazino[4,5-b]indole-1-acetic acid A solution of 1.15 g (2.7 mmol) of 5-methyl-4-oxo-3-phenyl-8-(phenylmethoxy)-3,5-dihydro-4H-pyridazino[4,5-b]indole-1-acetonitrile and of 1.54 g (39 mmol) of potassium hydroxide in a mixture of 10 ml of water and of 20 ml oF 2-methoxyethanol is heated at reflux. The mixture is extracted with dichloromethane, the aqueous phase is acidified and extracted with ethyl acetate, the organic phase is dried over sodium sulphate and the solvent is evaporated under reduced pressure. 0.38 g (0.86 mmol) of solid is isolated, which solid is used as is in the following stage.

8.2. 1-[2-(5-Methyl-4-oxo-3-phenyl-8-(phenylmethoxy)-3,5-dihydro-4H-pyridazino[4,5-b]indol-1-yl)-1-oxoethyl]pyrrolidine The preparation is carried out as in Example 3.2, from 0.38 g (0.86 mmol) of 5-methyl-4-oxo-3-phenyl-8-(phenylmethoxy)-3,5-dihydro-4H-pyridazino[4,5-b]indole-1-acetic acid. 0.35 g (0.7 mmol) of solid is obtained.

Melting point: 203–204° C.

EXAMPLE 9
(Compound No. 17)

N,N,5,8-Tetramethyl-4-oxo-3-phenyl-3,5-dihydro-4H-pyridazino[4,5-b]indole-1-acetamide

9.1. 1-(Chloromethyl)-5,8-dimethyl-3-phenyl-3,5-dihydro-4H-pyridazino[4,5-b]indol-4-one 50 ml of pyridine are added to a suspension of 9.5 g (29.7 mmol) of 1-(hydroxymethyl)-5,8-dimethyl-3-phenyl-3,5-dihydro-4H-pyridazino[4,5-b]indol-4-one in 600 ml of tetrahydrofuran heated to 60° C. 4.5 ml (59.4 mmol) of methanesulphonyl chloride are added and the mixture is left standing for 15 h at room temperature. 500 ml of dichloromethane are added, the precipitate is removed by filtration, separation is carried out by settling and the organic phase is washed with water. It is dried over sodium sulphate and the solvent is evaporated under reduced pressure. 5 g (14.8 mmol) of product are obtained, which product is used as is in the following stage.

9.2. 5,8-Dimethyl-4-oxo-3-phenyl-3,5-dihydro-4H-pyridazino[4,5-b]indole-1-acetonitrile A solution of 5 g (14.8 mmol) of 1-(chloromethyl)-5,8-dimethyl-3-phenyl-3,5-dihydro-4H-pyridazino[4,5-b]indol-4-one, of 2.7 g (55 mmol) of sodium cyanide and of 0.5 g (3 mmol) of sodium iodide in a mixture of 50 ml of dimethylformamide and of 30 ml of water is stirred for 2 h at 50° C. The mixture is left standing at room temperature and the precipitate is collected by filtration. It is washed with water and with pentane and is dried under reduced pressure. 3 g (9.1 mmol) of product are obtained, which product is used as is in the following stage.

9.3. 5,8-Dimethyl-4-oxo-3-phenyl-3,5-dihydro-4H-pyridazino[4,5-b]indole-1-acetic acid The preparation is carried out as in Example 1.7, from 3.4 g (10.4 mmol) of 5,8-dimethyl-4-oxo-3-phenyl-3,5-dihydro-4H-pyridazino[4,5-b]indole-1-acetonitrile. 2 g (5.8 mmol) of product are obtained, which product is used as is in the following stage.

9.4. N,N,5,8-Tetramethyl-4-oxo-3-phenyl-3,5-dihydro-4H-pyridazino[4,5-b]indole-1-acetamide The preparation is carried out as in Example 3.2, from 1 g (2.9 mmol) of 5,8-dimethyl-4-oxo-3-phenyl-3,5-dihydro-4H-pyridazino[4,5-b]indole-1-acetic acid. The product is recrystallized from propan-2-ol. 0.5 g (1.3 mmol) of solid is obtained.

Melting point: 209–210° C.

EXAMPLE 10
(Compound No. 43)

8-Fluoro-N,N-dimethyl-4-oxo-3-phenyl-3,5-dihydro-4H-pyridazino[4,5-b]indole-1-acetamide

10.1. Ethyl 2-(ethoxycarbonyl)-5-fluoro-α-oxo-1H-indole-3-acetate

A solution of 40 ml (313 mmol) of ethyl chloroglyoxylate and of 36 ml (313 mmol) of titanium tetrachloride in 1 l of dichloromethane is stirred for 15 min at room temperature. A solution of 50 g (241 mmol) of ethyl 5-fluoro-1H-indole-2-carboxylate in dichloromethane is added and the mixture is stirred for 2 h at room temperature. The mixture is poured into water and the organic phase is separated by settling, washed with dilute sodium hydroxide solution and dried over sodium sulphate. 31.5 g (102 mmol) of product are obtained, which product is used as is in the following stage.

10.2. Ethyl 8-fluoro-4-oxo-3-phenyl-3,5-dihydro-4H-pyridazino[4,5-b]indole-1-carboxylate The preparation is carried out as in Example 1.3, from 5 g (16.2 mmol) of ethyl 2-(ethoxycarbonyl)-5-fluoro-α-oxo-1H-indole-3-acetate and from 9.5 ml of phenylhydrazine in 150 ml of acetic acid. 3.9 g (11 mmol) of solid are isolated, which solid is used as is in the following stage.

10.3. Ethyl 8-fluoro-5-(methoxymethyl)-4-oxo-3-phenyl-3,5-dihydro-4H-pyridazino[4,5-b]indole-1-carboxylate A suspension of 3.9 g (11 mmol) of ethyl 8-fluoro-4-oxo-3-phenyl-3,5-dihydro-4H-pyridazino[4,5-b]indole-1-carboxylate in 200 ml of dimethylformamide is added to a suspension of 0.66 g (16 mmol) of sodium hydride in 100 ml of dimethylformamide. The mixture is stirred for 1.5 h at room temperature and a solution of 1.15 ml (14.3 mmol) of chloromethoxymethane in 10 ml of tetrahydrofuran is added. The mixture is stirred for 2 h, a solution of dilute hydrochloric acid is added and the precipitate is collected by filtration and dried under reduced pressure. 4.1 g (10.4 mmol) of solid are isolated, which solid is used as is in the following stage.

10.4. 8-Fluoro-1-(hydroxymethyl)-5-(methoxymethyl)-3-phenyl-3,5-dihydro-4H-pyridazino[4,5-b]indol-4-one The preparation is carried out as in Example 1.4, from 4.1 g (10.4 mmol) of ethyl 8-fluoro-5-(methoxymethyl)-4-oxo-3-phenyl-3,5-dihydro-4H-pyridazino[4,5-b]indole-1-carboxylate. 3.2 g (9 mmol) of solid are isolated, which solid is used as is in the following stage.

10.5. 1-(Bromomethyl)-8-fluoro-5-(methoxymethyl)-3-phenyl-3,5-dihydro-4H-pyridazino[4,5-b]indol-4-one 4.5 g (17.1 mmol) of triphenylphosphine are added to a solution of 3.2 g (9 mmol) of 8-fluoro-1-(hydroxymethyl)-5-(methoxymethyl)-3-phenyl-3,5-dihydro-4H-pyridazino[4,5-b]indol-4-one and of 6.3 g (19 mmol) of tetrabromomethane in 200 ml of dichloromethane. The mixture is stirred for 2 h, 50 ml of cyclohexane are added and the precipitate is collected by filtration and dried under reduced pressure. 2.9 g (7 mmol) of solid are isolated, which solid is used as is in the following stage.

10.6. 8-Fluoro-5-(methoxymethyl)-4-oxo-3-phenyl-3,5-dihydro-4H-pyridazino[4,5-b]indole-1-acetonitrile A two-phase mixture of 2.8 g (6.7 mmol) of 1-(bromomethyl)-8-fluoro-5-(methoxymethyl)-3-phenyl-3,5-dihydro-4H-pyridazino[4,5-b]indol-4-one, of 1.3 g (26 mmol) of sodium cyanide and of 0.23 g (0.7 mmol) of tetrabutylammonium bromide in 100 ml of dichloromethane and 100 ml of water is stirred vigorously for 12 h. The organic phase is separated, washed several times with water, dried over magnesium sulphate and concentrated under reduced pressure. Diethyl ether is added and the precipitate is collected by filtration and dried under reduced pressure. 2.1 g (5.8 mmol) of solid are isolated, which solid is used as is in the following stage.

10.7. 8-Fluoro-4-oxo-3-phenyl-3,5-dihydro-4H-pyridazino[4,5-b]indole-1-acetic acid The preparation is carried out as in Example 1.7, from 1.2 g (3.3 mmol) of 8-fluoro-5-(methoxymethyl)-4-oxo-3-phenyl-3,5-dihydro-4H-pyridazino[4,5-b]indole-1-acetonitrile. After filtration and drying, 1.1 g (3.2 mmol) of solid are isolated, which solid is used as is in the following stage.

10.8. 8-Fluoro-N,N-dimethyl-4-oxo-3-phenyl-3,5-dihydro-4H-pyridazino[4,5-b]indole-1-acetamide A suspension of 1.7 g (10.5 mmol) of 1,1'-carbonylbis-1H-imidazole and of 3 g (8.9 mmol) of 8-fluoro-4-oxo-3-phenyl-3,5-dihydro-4H-pyridazino[4,5-b]indole-1-acetic acid in 300 ml of tetrahydrofuran is stirred at 40° C. for 3 h. The mixture is cooled to room temperature, 10 ml of liquefied dimethylamine are added and the mixture is stirred for 2 h. After standing overnight, 300 ml of water are added and the precipitate is collected by filtration and recrystallized from dimethylformamide. 0.8 g (2.2 mmol) of solid is obtained.

Melting point: 289–290° C.

EXAMPLE 11
(Compound No. 52)

7-Chloro-N,N-diethyl-5-methyl-4-oxo-3-phenyl-3,5-dihydro-4H-pyridazino[4,5-b]indole-1-acetamide

11.1. Ethyl 6-chloro-1-methyl-1H-indole-2-carboxylate

The preparation is carried out as in Example 1.1, from 8.0 g (35.8 mmol) of ethyl 6-chloro-1H-indole-2-carboxylate, from 1.8 g of 60% sodium hydride and from 2.8 ml of iodomethane.

After reaction, the solvent is evaporated under reduced pressure and the residue is taken up in water. The mixture is extracted with dichloromethane, the organic phase is dried and filtered and the solvent is evaporated under reduced pressure. The residue is purified by chromatography on a column of silica gel. 8.5 g (35.8 mmol) of a white crystalline compound are isolated.

Melting point: 75.5–76.5° C.

11.2. Ethyl 6-chloro-2-(ethoxycarbonyl)-1-methyl-α-oxo-1H-indole-3-acetate 4 ml (36.4 mmol) of titanium(IV) chloride are added to a solution of 4 ml (36 mmol) of ethyl chlorooxoacetate in 100 ml of 1,2-dichloroethane. The reaction mixture is stirred for 30 min at room temperature, 7.8 g (32.8 mmol) of ethyl 6-chloro-1-methyl-1H-indole-2-carboxylate are then added and the reaction mixture is stirred for 4 hours at room temperature. The mixture is cooled and 200 ml of dichloromethane and 100 ml of water are added. The organic phase is separated by settling, washed with water, dried over sodium sulphate, filtered and concentrated under reduced pressure and the residue is purified by chromatography on a column of silica gel. 9.4 g (27.7 mmol) of product are isolated.

Melting point: 94–95° C.

11.3. Ethyl 7-chloro-5-methyl-4-oxo-3-phenyl-3,5-dihydro-4H-pyridazino[4,5-b]indole-1-carboxylate 4 ml (40.6 mmol) of phenylhydrazine are added at room temperature to a solution of 4.6 g (13.6 mmol) of ethyl 6-chloro-2-(ethoxycarbonyl)-1-methyl-α-oxo-1H-indole-3-acetate in 120 ml of acetic acid. The reaction mixture is stirred for 30 min at room temperature and then for 4 hours at reflux. The mixture is cooled and 350 ml of dichloromethane and 100 ml of water are added. The organic phase is separated by settling, washed with a saturated aqueous sodium hydrogencarbonate solution and then with water, dried over sodium sulphate, filtered and concentrated under reduced pressure and the residue is purified by chromatography on a column of silica gel. 4.1 g (10.7 mmol) of product are isolated.

Melting point: 216–218.5° C.

11.4. 7-Chloro-1-(hydroxymethyl)-5-methyl-3-phenyl-3,5-dihydro-4H-pyridazino[4,5-b]indol-4-one 2.5 g (66.1 mmol) of sodium borohydride are added to a solution of 4.04 g (10.6 mmol) of ethyl 7-chloro-5-methyl-4-oxo-3-phenyl-3,5-dihydro-4H-pyridazino[4,5-b]-indole-1-carboxylate in 150 ml of tetrahydrofuran. 2.25 ml of methanol are gradually added, with stirring, and then the mixture is heated at reflux for 5 hours. The mixture is poured onto an ice-cold 1 M hydrochloric acid solution and an insoluble product is separated by filtration on sintered glass, which product is washed with water and with diethyl ether and then dried. 3.3 g (9.7 mmol) of compound are isolated in the form of a white solid which is used as is in the following stage.

Melting point: 219–220.5° C.

11.5. 7-Chloro-5-methyl-4-oxo-3-phenyl-3,5-dihydro-4H-pyridazino[4,5-b]indole-1-carboxaldehyde 5.7 g (65.6 mmol) of manganese dioxide are added to a solution of 3.3 g (9.7 mmol) of 7-chloro-1-(hydroxymethyl)-5-methyl-3-phenyl-3,5-dihydro-4H-pyridazino[4,5-b]indol-4-one in 300 ml of dichloromethane and the reaction mixture is stirred for 24 hours at reflux. The mixture is cooled and filtered through a Teflon® membrane, the solid is rinsed with dichloromethane and then the filtrate is concentrated under reduced pressure. 2:88 g (8.53 mmol) of compound are isolated in the form of a white solid which is used as is in the following stage.

Melting point: 235–236° C.

11.6. 7-Chloro-5-methyl-4-oxo-3-phenyl-3,5-dihydro-4H-pyridazino[4,5-b]indole-1-acetonitrile 1.27 g (10.96 mmol) of potassium 1,1-dimethylethoxide are added, in small portions, to a solution of 2.14 g (10.96 mmol) of (4-methylbenzenesulphonyl)methyl isocyanide in 50 ml of 1,2-dimethoxyethane, the reaction mixture is stirred for 30 min at −60° C., 2.88 g (8.53 mmol) of 7-chloro-5-methyl-4-oxo-3-phenyl-3,5-dihydro-4H-pyridazino[4,5-b] indole-1-carboxaldehyde are added and the reaction mixture is stirred for 3 hours 30 min at −60° C. 9 ml of methanol are added and the reaction mixture is further stirred for 30 min at room temperature and for 1 hour at reflux. The mixture is cooled and concentrated under reduced pressure, water, 5 ml of acetic acid and 200 ml of dichloromethane are added to the residue, the organic phase is separated by settling and the aqueous phase is extracted with dichloromethane. The organic phases are combined, washed with water, dried over sodium sulphate, filtered and concentrated under reduced pressure and the residue is purified by chromatography on a column of silica gel. 1.87 g (5.36 mmol) of compound are isolated in the form of a white solid which is used as is in the following stage.

Melting point: 305–315° C.

11.7. Methyl 7-chloro-5-methyl-4-oxo-3-phenyl-3,5-dihydro-4H-pyridazino[4,5-b]indole-1-acetate Hydrogen chloride is added to a solution of 1.83 g (5.25 mmol) of 7-chloro-5-methyl-4-oxo-3-phenyl-3,5-dihydro-4H-pyridazino[4,5-b]indole-1-acetonitrile in 250 ml of methanol until the solution is saturated and the reaction mixture is stirred for 4 hours at reflux. The mixture is cooled, the reaction mixture is concentrated under reduced pressure and 25 ml of water and 25 ml of methanol are added to the residue. After stirring, the insoluble product is collected by filtration, washed with water and with diethyl ether, dried and purified by chromatography on a column of silica gel. 1.00 g (2.62 mmol) of compound is isolated in the form of a white solid.

Melting point: 188.5–190° C.

11.8. 7-Chloro-N,N-diethyl-5-methyl-4-oxo-3-phenyl-3,5-dihydro-4H-pyridazino[4,5-b]indole-1-acetamide 0.41 ml (4 mmol) of diethylamine is added at 0° C. under argon to a solution of 2 ml (4 mmol) of trimethylaluminium (2M in toluene) in 30 ml of toluene, the reaction mixture is stirred for 20 min at room temperature, 0.095 g (0.25 mmol) of methyl 7-chloro-5-methyl-4-oxo-3-phenyl-3,5-dihydro-4H-pyridazino[4,5-b]-indole-1-acetate is added and the reaction mixture is stirred for 4 h at reflux. The mixture is cooled to 4° C., 3 ml of water and dichloromethane are added, the solution is filtered and the filtrate is concentrated under reduced pressure. Water, 1M hydrochloric acid and 150 ml of dichloromethane are added to the residue, the organic phase is separated, washed with water, dried over sodium sulphate, filtered and concentrated under reduced pressure and the residue is purified by chromatography on a column of silica gel. After recrystallization from diethyl ether, 0.10 g (0.24 mmol) of compound is isolated in the form of a white solid with a fluffy appearance.

Melting point: 167–168° C.

The chemical structures and the physical properties of some compounds according to the invention are illustrated in the following table.

TABLE (I)

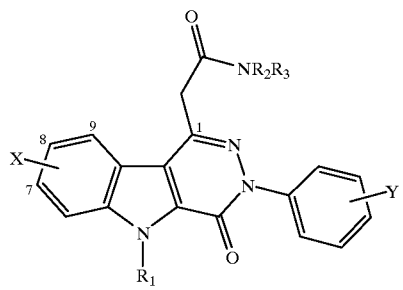

| No. | X | Y | R₁ | NR₂R₃ | M.p.(° C.) |
|---|---|---|---|---|---|
| 1 | 8-F | H | Me | NMe₂ | 248–249 |
| 2 | 8-F | H | Me | NHMe | 303–304 |
| 3 | 8-F | H | Me | NHCH₂Ph | 298–299 |
| 4 | 8-F | H | Me | pyrrolid | 268–269 |
| 5 | 8-F | H | Me | piperid | 248–249 |
| 6 | 8-Cl | H | Me | NHMe | 314–315 |
| 7 | 8-Cl | H | Me | NMe₂ | 250–251 |
| 8 | 8-F | H | Et | NHMe | 310–312 |
| 9 | 8-F | H | Et | NMe₂ | 183–184 |
| 10 | 8-F | H | Me | NHEt | 291–292 |
| 11 | 9-Br | H | Me | NHMe | 267–268 |
| 12 | 8-F | H | Me | NHPr | 290–291 |
| 13 | 8-F | H | Me | morph | 259–260 |
| 14 | 8-F | H | Me | 4-Me-piperaz | 233–234 |
| 15 | 8-OMe | H | Me | NMe₂ | 194–195 |
| 16 | 8-OMe | H | Me | NHMe | 258–259 |
| 17 | 8-Me | H | Me | NMe₂ | 209–210 |
| 18 | 8-Me | H | Me | NHMe | 268–269 |
| 19 | 8-Me | H | Me | pyrrolid | 216–217 |

TABLE-continued (I)

| No. | X | Y | R₁ | NR₂R₃ | M.p.(° C.) |
|---|---|---|---|---|---|
| 20 | 8-F | H | Et | pyrrolid | 229–230 |
| 21 | 8-F | H | Me | azetid | 236–237 |
| 22 | 8-F | H | Me | thiazolid | 246–247 |
| 23 | 8-OCH₂Ph | H | Me | pyrrolid | 203–204 |
| 24 | 8-F | H | Me | 3-EtO-pyrrolid | 204–206 |
| 25 | 8-Cl | H | Me | pyrrolid | 261–262 |
| 26 | H | H | Me | pyrrolid | 214–215 |
| 27 | H | H | Me | NMe₂ | 214–215 |
| 28 | H | H | Me | NHMe | 262–263 |
| 29 | 8-F | H | Me | NEt₂ | 179–180 |
| 30 | 8-F | H | Me | NMeEt | 231–232 |
| 31 | 9-Br | H | Me | pyrrolid | 209–210 |
| 32 | 8-F | H | Et | NMeEt | 167–168 |
| 33 | 8-F | H | Et | azetid | 186–187 |
| 34 | 8-F | 4-Cl | Me | pyrrolid | 241–242 |
| 35 | 8-F | 4-Cl | Me | NMe₂ | 243–244 |
| 36 | 8-F | 3-Cl | Me | NHMe | 315–316 |
| 27 | 8-F | 4-Cl | Me | NHMe | 290–291 |
| 38 | 9-Me | H | Me | pyrrolid | 214–215 |
| 39 | 8-F | 3-Cl | Me | pyrrolid | 210–211 |
| 40 | 8-F | 2-Cl | Me | pyrrolid | 248–249 |
| 41 | 8-F | H | H | pyrrolid | 242–243 |
| 42 | 8-F | 2-Cl | Me | NMe₂ | 226–227 |
| 43 | 8-F | H | H | NMe₂ | 289–290 |
| 44 | 9-F | H | Me | NHMe | 298–299 |
| 45 | 8-F | H | Et | NH₂ | >260 |
| 46 | 8-F | H | Pr | NMe₂ | 167–168 |
| 47 | 9-F | H | Me | pyrrolid | 194–195 |
| 48 | 9-F | H | Me | NMe₂ | 186–187 |
| 49 | 8-F | 4-OMe | Et | NMe₂ | 197–198 |
| 50 | 8-F | 4-OH | Et | NMe₂ | 270 |
| 51 | 7-Cl | H | Me | NMe₂ | 229.5–230 |
| 52 | 7-Cl | H | Me | NEt₂ | 167–168 |
| 53 | 7-Cl | H | Me | pyrrolid | 260–263 |
| 54 | 7-Cl | H | Me | morph | 273.5–274.5 |
| 55 | 7-Cl | 3-Me | Me | NMe₂ | 204–205.5 |
| 56 | 7-Cl | 3-Me | Me | NEt₂ | 200.5–201 |
| 57 | 7-Cl | 3-Me | Me | pyrrolid | 268–269.5 |
| 58 | 7-Cl | 3-Cl | Me | NMe₂ | 231–232 |
| 59 | 7-Cl | 3-Cl | Me | NEt₂ | 202.5–203 |
| 60 | 7-Cl | 3-Cl | Me | pyrrolid | 257–258.5 |
| 61 | 7-Cl | 3-Cl | Me | piperid | 218–219 |
| 62 | 7-Cl | 2-Cl | Me | NMe₂ | 253–255 |
| 63 | 7-Cl | 2-Cl | Me | NEt₂ | 206–208 |
| 64 | 7-Cl | 2-Cl | Me | pyrrolid | 295–297 |
| 65 | 7-Cl | 4-Cl | Me | NMe₂ | 235–237 |
| 66 | 7-Cl | 4-Cl | Me | NEt₂ | 223.5–224.5 |
| 67 | 7-Cl | 4-Cl | Me | pyrrolid | 265–266 |
| 68 | 7-Cl | 3-OMe | Me | NMe₂ | 200.5–202.5 |
| 69 | 7-Cl | 3-OMe | Me | NEt₂ | 201–202 |
| 70 | 7-Cl | 3-OMe | Me | pyrrolid | 240–242 |
| 71 | 7-Cl | 3-NO₂ | Me | NMe₂ | 275–277.5 |
| 72 | 7-Cl | 3-NO₂ | Me | NEt₂ | 228–228.5 |
| 73 | 7-Cl | 3-NO₂ | Me | pyrrolid | 261–263 |
| 74 | 7-Cl | 3-F | Me | NMe₂ | 225–226.5 |
| 75 | 7-Cl | 3-F | Me | NEt₂ | 171–172 |
| 76 | 7-Cl | 3-F | Me | pyrrolid | 270–271.5 |
| 77 | 7-Cl | 3,5-(Cl)₂ | Me | NEt₂ | 239–240.5 |
| 78 | 7-Cl | 4-Cl | Me | NMeEt | 216.5–217.5 |

Key

"Me", "Et", "Pr" and "Ph" respectively denote a methyl, ethyl, propyl and phenyl group.

"azetid", "pyrrolid", "piperid", "morph", "piperaz" and "thiazolid" respectively denote an azetidinyl, pyrrolidinyl, piperidinyl, morpholinyl, piperazinyl and 1,3-thiazolidinyl group.

The compounds of the invention were subjected to pharmacological tests which demonstrated their advantage as substances having therapeutic activities.

Study of Membrane Binding with Respect to $\omega_1$ Receptors of the Cerebellum (Type 1 Benzodiazepine) and $\omega_2$ Receptors of the Spinal Cord (Type 2 Benzodiazepine)

The affinity of the compounds for the $\omega_1$ receptors of the cerebellum and $\omega_2$ receptors of the spinal cord was determined according to a variant of the method described by S. Z. Langer and S. Arbilla in *Fund. Clin. Pharmacol.*, 2, 159–170 (1988), with the use of [$^3$H]flumazenil instead of [$^3$H]diazepam as radioligand.

The cerebellar or spinal cord tissue is homogenized for 60 s in 120 or 30 volumes, respectively, of ice-cold buffer (50 mM Tris-HCl, pH 7.4, 120 mM NaCl, 5 mM KCl) and then, after dilution to 1/3, the suspension is incubated with [$^3$H] flumazenil (specific activity 78 Ci/mmol, New England Nuclear) at a concentration of 1 nM and with the compounds of the invention at different concentrations, in a final volume of 525 μl. After 30 minutes of incubation at 0° C., the samples are filtered under reduced pressure on Whatman GF/B® filters and washed immediately with ice-cold buffer. The specific binding of [-H]flumazenil is determined in the presence of 1 μM unlabelled diazepam. The data are analysed according to standard methods and the $IC_{50}$ concentration, the concentration which inhibits by 50% the binding of [$^3$H]flumazenil, is calculated. The $IC_{50}$ values of the most closely related compounds of the invention lie between 5 and 1000 nM for the $\omega_1$ receptors of the cerebellum and between 20 and 1000 nM for the $\omega_2$ receptors of the spinal cord.

Study of the Anxiolytic Activity

Drink Intake Conflict Test

The anxiolytic activity is evaluated in rats in the drink intake conflict test according to the method described by J. R. Vogel, B. Beer and D. E. Clody in *Psychopharmacologia* (Berl.), 21, 1–7 (1971).

After being deprived of water for 48 h, the rat is placed in a soundproof chamber equipped with a water pipette connected to an anxiometer which delivers a mild electric shock every 20 licks. The number of shocks received is automatically counted over 3 minutes and makes it possible to evaluate the anxiolytic activity of the tested compounds. The results are expressed by the minimum effective dose (MED), the dose which produces a significant increase in the number of shocks received, with respect to the number observed in the control animals.

The MED values of the most active compounds lie, in this test, between 0.1 and 10 mg/kg via the intraperitoneal or oral route.

Test in a Heightened Cross-shaped Maze

The protocol of this test is a modification of that described by S. Pellow and S. File in *Pharmacol. Biochem. Behav.* (1986), 24, 525–529.

After a period of accustomization to the experimental room lasting approximately 24 h, the rats are placed individually on the central platform, the muzzle directed towards one of the closed arms, and observed for 4 min using a video camera. The time spent by the animal in the open arms, the number of entries into the closed arms and into the open arms, the number of attempts to enter the open arms, followed by an avoidance response, and the exploration of the edges in the open arms are recorded. The results are expressed for each animal: 1) as percentage of passages into the open arms relative to the total number of entries into the four arms of the apparatus, 2) as percentage of time spent in the open arms relative to the total duration of the test (4 min), 3) as total number of abortive attempts made by the animal, 4) as total number of explorations.

The products under study are administered intraperitoneally or orally at increasing doses. The results are expressed by the minimum effective dose (MED) which produces either a significant increase (activity in the open arms) or a significant decrease (attempts) relative to the performance observed in the control animals.

The MED values of the most active compounds lie, in this test, between 0.1 and 20 mg/kg via the intraperitoneal or oral route.

Study of the Hypnotic Activity

The sedative or hypnotic activity of the compounds was determined by observing their action on the rat's electrocorticogram, according to the method described by H. Depoortere, *Rev. E.E.G. Neurophysiol.*, 10, 3, 207–214 (1980) and by H. Depoortere and M. Decobert, *J. Pharmacol.*, (Paris), 14, 2, 195–265 (1983).

The products under study were administered intraperitoneally at increasing doses. The most active compounds induce sleep patterns at doses ranging from 0.1 to 30 mg/kg.

Study of the Anticonvulsant Activity

Activity with Respect to Clonic Convulsions Induced in Rats by Injection of Pentetrazol The protocol of this test is a modification of that described by E. A. Swinyard and J. H. Woodhead in *Antiepileptic Drugs*, Raven Press, New York, 111–126 (1982).

The test products are administered to the animals intraperitoneally 30 min before an intravenous injection of 20 mg/kg of pentetrazol. Immediately after the injection, the number of animals exhibiting clonic convulsions is noted over 5 min.

The results are expressed as the $AD_{50}$, the dose which protects 50% of the animals, calculated according to the method of J. T. Lichtfield and F. Wilcoxon (*J. Pharm. Exp. Ther.* (1949), 96, 99–113) on the basis of 3 or 4 doses each administered to a group of 8 to 10 rats.

The $AD_{50}$ values of the most active compounds lie between 0.1 and 10 mg/kg via the intraperitoneal or oral route.

Study of the Anticonvulsant Activity

Activity with Respect to Isoniazid-induced Convulsions in Mice

The intrinsic activity of the compounds is determined by the latency time of onset of convulsions induced by the subcutaneous administration of isoniazid (800 mg/kg) simultaneously with the test compound injected intraperitoneally, according to the protocol described by G. Perrault, E. Morel, D. Sanger and B. Zivkovic in *Eur. J. Pharmacol.*, 156, 189–196 (1988). The results are expressed as the $AD_{50}$, the dose which produces 50% of the maximum effect, relative to the control animals, determined on the basis of 3 or 4 doses each administered to a group of 8 to 10 mice. The $AD_{50}$ values of the most active compounds lie, in this test, between 1 and 20 mg/kg via the intraperitoneal route and, depending on the compounds, the maximum effect can be as much as 400%.

The results of the tests performed on the compounds of the invention show that, in vitro, they displace [$^3$H] flumazenil from its $\omega_1$ specific binding sites in the cerebellum and $\omega_2$ specific binding sites in the spinal cord; they exhibit an affinity for the $\omega_1$ and $\omega_2$ sites situated in the $GABA_A$—$\omega$ sites—chlorine channel macromolecular complex.

In vivo, they behave as full or partial agonists with respect to these receptor subtypes. They possess anxiolytic, hypnotic and anticonvulsant properties.

Consequently, they can be used for the treatment of complaints associated with disorders of GABAergic transmission, such as anxiety, sleep disorders, epilepsy, spasticity, muscle contractures, cognitive disorders, withdrawal disorders related to alcoholism, tobacco or drugs, and the like.

They can also be used for the treatment of Parkinson's disease and all types of extrapyramidal syndromes. Finally, they can be used in premedication and as general anaesthetics for the induction and/or maintenance of anaesthesia, or as local anaesthetics, optionally in combination with other anaesthetics and/or muscle relaxants and/or analgesics.

They can be presented in any composition form appropriate for enteral, parenteral or transdermal administration, such as tablets, dragees, capsules, including hard gelatin capsules, suspensions or solutions to be swallowed or injected, such as syrups or phials, transdermal patches, and the like, in combination with suitable excipients, containing a dose which permits a daily administration of 1 to 1000 mg of active substance

What is claimed is:

1. A compound corresponding to the general formula (I)

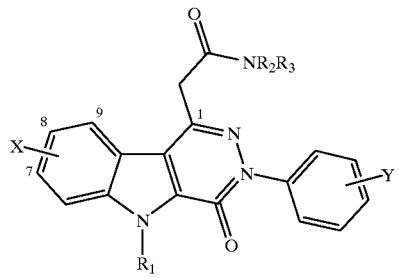

in which

X represents a hydrogen or halogen atom or a methyl, methoxy or phenylmethoxy group, Y represents a hydrogen atom, 1 or 2 halogen atoms or a hydroxyl, methoxy, nitro or methyl group, $R_1$ represents a hydrogen atom or a $(C_1-C_4)$alkyl group, $R_2$ and $R_3$ each represent, independently of one another, a hydrogen atom, a $(C_1-C_4)$alkyl group or a phenylmethyl group, or else $R_2$ and $R_3$ form, with the nitrogen atom which carries them, an azetidinyl, pyrrolidinyl, 3-ethoxypyrrolidinyl, piperidinyl, morpholinyl, 4-methylpiperazinyl or 1,3-thiazolidinyl group.

2. A compound according to claim 1, wherein X is in the 8 or 9 position and represents a hydrogen or halogen atom, Y represents a hydrogen atom, $R_1$ represents a methyl or ethyl group, $R_2$ represents a hydrogen atom or a methyl group and $R_3$ represents a methyl group or else $R_2$ and $R_3$ form, with the nitrogen atom which carries them, an azetidinyl or pyrrolidinyl ring.

3. A pharmaceutical composition, which comprises a compound according to claim 1 in combination with an excipient.

4. A method for the treatment of anxiety; sleep disorder; epilepsy; spasticity; or muscle contracture, which comprises administering to a host in need of the treatment an effective amount of a compound according to claim 1.

5. A method for the treatment of an extrapyramidal syndrom, which comprises administering to a host in need of the treatment an effective amount of a compound according to claim 1.

6. A method for inducing or maintaining anaesthesia, which comprises administering to a host in need of the treatment an effective amount of a compound according to claim 1.

7. A method as claimed in claim 6, which comprises administering with the compound according to claim 1 another compound which is an anaesthetic, a muscle relaxant, or an analgesic.

* * * * *